United States Patent
Liu et al.

(10) Patent No.: US 12,112,475 B2
(45) Date of Patent: Oct. 8, 2024

(54) METHOD AND SYSTEM FOR PREDICTING TUMOR MUTATION BURDEN (TMB) IN TRIPLE NEGATIVE BREAST CANCER (TNBC) BASED ON NUCLEAR SCORES AND HISTOPATHOLOGICAL WHOLE SLIDE IMAGES (WSIs)

(71) Applicant: Wuhan University, Wuhan (CN)

(72) Inventors: Juan Liu, Wuhan (CN); Yuqi Chen, Wuhan (CN); Jing Feng, Wuhan (CN)

(73) Assignee: WUHAN UNIVERSITY, Wuhan (CN)

( * ) Notice: Subject to any disclaimer, the term of this patent is extended or adjusted under 35 U.S.C. 154(b) by 386 days.

(21) Appl. No.: 17/659,914

(22) Filed: Apr. 20, 2022

(65) Prior Publication Data

US 2023/0153994 A1     May 18, 2023

(30) Foreign Application Priority Data

Nov. 11, 2021    (CN) .......................... 202111333910.8

(51) Int. Cl.
*G06T 7/00*     (2017.01)
*G06T 7/11*     (2017.01)
(Continued)

(52) U.S. Cl.
CPC .............. *G06T 7/0012* (2013.01); *G06T 7/11* (2017.01); *G06V 10/764* (2022.01);
(Continued)

(58) Field of Classification Search
CPC ..................... G06T 7/0012; G06T 7/11; G06T 2207/10056; G06T 2207/20036;
(Continued)

(56) References Cited

U.S. PATENT DOCUMENTS 11,321,842 B1 *   5/2022   Tiwari ................... G06T 7/0014
11,954,596 B2 *   4/2024   Song ....................... G06V 10/82
(Continued)

OTHER PUBLICATIONS

Adams et al. "Abstract OT1-03-20: A Phase 2 Study if Pembrolizumab (MK-3475) Monotherapy for Metastatic Triple-Negative Breast Cancer (mTNBC): Keynote-086", Cancer Research, Feb. 15, 2016, vol. 76, Issue 4 Supplement (1 page).
(Continued)

*Primary Examiner* — Dhaval V Patel
(74) *Attorney, Agent, or Firm* — Westman, Champlin & Koehler, P.A.

(57) ABSTRACT

Provided is a method and system for predicting tumor mutation burden (TMB) in triple negative breast cancer (TNBC) based on nuclear scores and histopathological whole slide images (WSIs). The method includes the following steps: first, screening the histopathological WSIs of TNBC; calculating a TMB value of each patient according to gene mutation of each patient with TNBC, and dividing the TMB values into two groups with high and low TMB according to a set threshold; dividing the histopathological WSIs of TNBC into patches of a set size; screening a certain number of patches with high nuclear scores according to a nuclear score function; then building a convolutional neural network (CNN) classification model, and stochastically initializing parameters in the CNN classification model; and finally, putting the screened patches into the built CNN classification model for training, so as to automatically predict high or low TMB with the histopathological WSIs of TNBC.

10 Claims, 6 Drawing Sheets

(51) Int. Cl.
*G06V 10/764* (2022.01)
*G06V 10/774* (2022.01)
*G06V 10/82* (2022.01)
*G16H 30/40* (2018.01)
*G16H 50/20* (2018.01)

(52) U.S. Cl.
CPC ............ *G06V 10/774* (2022.01); *G06V 10/82* (2022.01); *G16H 30/40* (2018.01); *G16H 50/20* (2018.01); *G06T 2207/10056* (2013.01); *G06T 2207/20036* (2013.01); *G06T 2207/20081* (2013.01); *G06T 2207/20084* (2013.01); *G06T 2207/30024* (2013.01); *G06T 2207/30068* (2013.01); *G06T 2207/30096* (2013.01); *G06V 2201/03* (2022.01)

(58) Field of Classification Search
CPC . G06T 2207/20081; G06T 2207/20084; G06T 2207/30024; G06T 2207/30068; G06T 2207/30096; G06T 7/136; G06T 2207/10024; G06T 2207/20021; G06V 10/764; G06V 10/774; G06V 10/82; G06V 2201/03; G06V 20/695; G06V 20/698; G16H 30/40; G16H 50/20; G16H 50/30; G16B 20/00; G16B 40/20; G16B 20/50; G16B 40/00; A61B 5/7264; A61B 5/7267; A61B 5/7275; G06F 18/241; G06N 3/045; G06N 3/08
See application file for complete search history.

(56) References Cited

U.S. PATENT DOCUMENTS

| | | | | |
|---|---|---|---|---|
| 2022/0207726 | A1* | 6/2022 | Ren | G06V 10/267 |
| 2022/0319704 | A1* | 10/2022 | Feng | G06V 10/7753 |
| 2023/0177682 | A1* | 6/2023 | Xiao | G06T 7/11 |
| | | | | 382/133 |

OTHER PUBLICATIONS

Alexandrov et al. "Signatures of Mutational Processes in Human Cancer", Nature, Aug. 22, 2013, vol. 500, pp. 415-421.
Banerji et al. "Sequence Analysis of Mutations and Translocations Across Breast Cancer Subtypes", Nature, Jun. 21, 2012, vol. 486, pp. 405-409.
Barroso-Sousa et al. "Tumor Mutational Burden and PTEN Alterations as Molecular Correlates of Response to PD-1/L1 Blockade in Metastatic Triple-Negative Breast Cancer", Clinical Cancer Research, Jun. 1, 2020, vol. 26, No. 11, pp. 2565-2572.
Chen et al. "Classification and Mutation Prediction Based on Histopathology H&E Images in Liver Cancer Using Deep Learning", Nature Partner Journals: Precision Oncology, 2020, vol. 14, 7 pages.
Coudray et al. "Classification and Mutation Prediction from Non-Small Cell Lung Cancer Histopathology Images Using Deep Learning", Nature Medicine, Oct. 2018, vol. 24, pp. 1559-1567.
Samstein et al. "Tumor Mutational Load Predicts Survival After Immunotherapy Across Multiple Cancer Types", Nature Genetics, Feb. 2019, vol. 51, pp. 202-206.
Schmid et al. "Atezolizumab and Nab-Paclitaxel in Advanced Triple-Negative Breast Cancer", The New England Journal of Medicine, Nov. 29, 2018, vol. 379, No. 22, pp. 2108-2121.
Schmid et al. "Impassion130: Updated Overall Survival (OS) From a Global, Randomized, Double-Blind, Placebo-Controlled, Phase III Study of Atezolizumab (atezo) + nab-Paclitaxel (nP) in Previously Untreated Locally Advanced or Metastatic Triple-Negative Breast Cancer (mTNBC)" Meeting Abstract, Journal of Clinical Oncology, 2019 (1 page).
Sharma, P. "Biology and Management of Patients With Triple-Negative Breast Cancer", The Oncologist, Jul. 11, 2016, vol. 21, pp. 1050-1062.
Sung et al. "Global Cancer Statistics 2020: Globocan Estimates of Incidence and Mortality Worldwide for 36 Cancers in 185 Countries", CA: A Cancer Journal for Clinicians, May/Jun. 2021, vol. 71, No. 3, pp. 209-249.
Valero et al. "Response Rates to Anti-PD-1 Immunotherapy in Microsatellite-Stable Solid Tumors With 10 or More Mutations Per Megabase", JAMA Oncology, May 2021, vol. 7, No. 5, pp. 739-743.
Wang et al. "Triple Negative Breast Cancer in Asia: An Insider's View", Cancer Treatment Reviews, vol. 62, 2018, pp. 29-38.
Yarchoan et al. "Tumor Mutational Burden and Response Rate to PD-1 Inhibition", Author Manuscript, HHS Public Access, Jun. 5, 2019 (4 pages) (based on N. Engl. J.Med., vol. 377, No. 25, Dec. 21, 2017, pp. 2500-2501).
The Nobel Assembly at Karolinska Institutet, "Press Release: The Nobel Prize in Physiology or Medicine 2018", Oct. 1, 2018, 5 pages.
National Institute of Health/Hoffmann-LaRoche, "A Study of Atezolizumab in Combination With Nab-Paclitaxel Compared With Placebo With Nab-Paclitaxel for Participants With Previously Untreated Metastatic Triple-Negative Breast Cancer (IMpassion130)", U.S. National Library of Medicine, Oct. 18, 2021, 4 pages.

* cited by examiner

METHOD AND SYSTEM FOR PREDICTING TUMOR MUTATION BURDEN (TMB) IN TRIPLE NEGATIVE BREAST CANCER (TNBC) BASED ON NUCLEAR SCORES AND HISTOPATHOLOGICAL WHOLE SLIDE IMAGES (WSIs)

CROSS REFERENCE TO RELATED APPLICATION

This patent application claims the benefit and priority of Chinese Patent Application No. 202111333910.8, filed on Nov. 11, 2021 the disclosure of which is incorporated by reference herein in its entirety as part of the present application.

TECHNICAL FIELD

The present disclosure relates to the cross field of machine learning and medicine, and in particular, relates to a method and system for predicting tumor mutation burden (TMB) in triple-negative breast cancer (TNBC) based on nuclear scores and histopathological whole slide images (WSIs), belonging to the application of a machine learning neural network model in medical diagnosis.

BACKGROUND ART

According to the report of the International Agency for Research on Cancer (AIRC), it is estimated that there will be 19.3 million new cancer cases and nearly 10 million cancer deaths in 2020. Breast cancer in women has surpassed lung cancer as the most commonly diagnosed cancer, with an estimated 2.3 million new cases (11.7%), seriously jeopardizing women's health. TNBC accounts for approximately 15% of breast cancer cases in the United States and 10-17% of breast cancer cases in Asia. With advances in medical technology, effective treatments have been found for many subtypes of breast cancer. However, there is still a lack of effective treatments for patients with TNBC. Due to the lack of expression of estrogen receptor (ER), progestogen receptor (PR), and human epidermal growth factor receptor 2 (HER2), they cannot benefit from endocrine therapy and anti-HER2-targeted therapy, which is highly aggressive and prone to distant metastasis and local recurrence. Therefore, patients with TNBC have a high recurrence rate and poor prognosis after standard treatment. Although traditional surgical treatment, chemotherapy, radiotherapy, and targeted drug therapy have some effects, they are far from enough to satisfy treatment demand. In recent years, tumor immunotherapy can achieve the "clinical cure" effect in advanced cancer, which has become a focus area of cancer research, and it has shown very effective therapeutic effect in many cancers. In October 2018, American immunologist James Allison and Japanese immunologist Tasuku Honjo were awarded the Nobel Prize in Physiology or Medicine for their contributions to tumor immunology, and their research provided a way to fight tumor cells by stimulating the original ability of the immune system. This award has laid the importance of tumor immunotherapy. Checkpoint therapy has completely changed the method of cancer treatment and fundamentally changed human's view of cancer treatment. Immunotherapy has become a new generation of tumor treatment methods after surgery, chemotherapy, radiotherapy, and tumor-targeted therapy.

Immunotherapy has achieved excellent results in patients with TNBC, such as the Impassion 130 study presented at the European Society for Medical Oncology (ESMO) Congress 2018, and the phase III KEYNOTE-522 study reported at the ESMO Congress 2019. In addition, the U.S. Food and Drug Administration (FDA) granted accelerated approval in 2019 to the PD-L1 monoclonal antibody atezolizumab developed by Roche's GENETECH in combination with chemotherapy for the first-line treatment of unresectable locally advanced or metastatic PD-L1-positive TNBC, and this is the first approved immunotherapy for TNBC. In Nov. 13, 2020, the FDA approved Keytruda (pembrolizumab) in combination with chemotherapy for the treatment of patients with locally recurrent or metastatic TNBC whose tumors express the PD-L1 biomarker.

Although immunotherapy can achieve great therapeutic effects, not all patients can benefit from immunotherapy, and screening patients suitable for immunotherapy has become a key clinical problem. Doctors and researchers are also committed to looking for biomarkers that can screen patients in recent years, and they found that TMB is an effective marker. Higher TMB indicates a greater number of neoantigens produced and more recognition sites used as immunotherapy to make the therapeutic effect better. Screening suitable patients with TMB for lung cancer treatment has been written into the National Comprehensive Cancer Network (NCNN) guidelines. In TNBC, it is found that TNBC has a higher mutation rate than other subtypes of breast cancer. YARCHOAN et al. found a positive correlation between TMB and the efficacy of immune checkpoint inhibitors (ICIs) in 27 cancers including breast cancer. Samstein et al. studied immunotherapy data in 1662 patients with 10 cancers including breast cancer and demonstrated for the first time in multiple cancers that patients with high TMB had better survival after receiving immunotherapy, and high TMB was positively correlated with better overall survival (OS). Data from a phase II TAPUR study on TMB in evaluation of pembrolizumab monotherapy in metastatic breast cancer, presented at the 2019 American Society of Clinical Oncology (ASCO) meeting, confirmed that patients with advanced breast cancer with high TMB could benefit from pembrolizumab therapy. The latest data from the KEYNOTE-119 study at the 2020 ASCO meeting showed that TMB is an effective indicator for predicting the efficacy of pembrolizumab in combination with chemotherapy in the TNBC-predominant population. Barroso-Sousa et al. also evaluated the association of TMB with the therapeutic effect of mTNBC anti-PD-1/PD-L1 therapy in patients with metastatic TNBC and showed that high TMB was significantly associated with longer PFS. Valero et al. studied the relationship between TMB and immunotherapy effect in 1678 patients with a total of 16 cancer tumors, which showed that the response rates (RRs) of patients with high TMB tumors were higher than those with low TMB tumors in 11 cancer types including breast cancer. These studies indicate that TMB can be used as a biomarker for screening patients with TNBC suitable for immunotherapy.

The clinical measurement of TMB is mainly based on Whole Exome Sequencing (WES) technology, but this sequencing method is costly, complicated, and time-consuming. It is difficult to achieve in general hospitals and lacks universality, limiting the role of immunotherapy. In addition, although there are studies on the use of histopathological images to predict TMB in other cancer types, there are some problems in these studies: using all patches to predict TMB is noisy, resulting in low accuracy, and patches based on tumor areas labeled by pathologists are used to predict TMB, which relies too much on the labeling of the pathologist.

SUMMARY

The present disclosure provides a method and system for predicting TMB in TNBC based on nuclear scores and histopathological WSIs, so as to solve or at least partially solve the technical problem of low prediction accuracy in the methods in the prior art.

In order to solve the above technical problem, a first aspect of the present disclosure provides a method for predicting TMB in TNBC based on nuclear scores and histopathological WSIs, including the following steps:

S1: screening the histopathological WSIs of TNBC from histopathological images of breast cancer;

S2: calculating a TMB value of each patient according to gene mutation of each patient with TNBC, and dividing the TMB values into two groups with high and low TMB according to a set threshold, denoted as TMB-H and TMB-L respectively, as a label corresponding to the WSI of each patient;

S3: dividing the WSIs into patches of a set size and performing preprocessing;

S4: screening patches with the nuclear scores meeting a threshold from the preprocessed patches according to a nuclear score function;

S5: building a convolutional neural network (CNN) classification model, and stochastically initializing parameters in the CNN classification model;

S6: standardizing color of the patches with the nuclear scores meeting the threshold, and inputting the patches after color standardization and corresponding labels into the CNN classification model to train a TMB classifier, where each patch belongs to the corresponding WSI, and the label corresponding to the patch is the label of the WSI corresponding to the patch;

S7: predicting the TMB in the TNBC using the trained TMB classifier.

In one implementation, a process of calculating a TMB value of each patient according to gene mutation of each patient with TNBC in step S2 may include: dividing tumors with nonsynonymous mutations in a somatic protein coding region of the patient by a total length of the protein coding region to obtain the TMB value of each patient, in mutations/mb, to characterize a density of distribution of nonsynonymous mutations in the protein coding region.

In one implementation, when the TMB values are divided into two groups with high and low TMB in step S2, a median division method may be used, and the threshold is recorded as M. When the TMB value of the patient is greater than M, the patient may be in the TMB-H group, otherwise, the patient may be in the TMB-L group.

In one implementation, step S3 may include:

first, selecting the number of layers of WSI, and saving the images of the set size successively based on this layer, so as to cut the image into patches;

second, removing blank and irregular patches from the cut patches, where a method for removing the blank patches may be: calculating a pixel mean of each patch, and when the pixel mean of the patch is less than the set threshold, retaining the patch, otherwise discarding the patch; and a method for removing the irregular patches may be: calculating whether each patch has a length and width equal to a set patch size, and if the length and width are equal to the set patch size, retaining the patch, otherwise discarding the patch.

In one implementation, step S4 may include:

S4.1: converting an RGB image to HED space and extracting a value of an H channel;

S4.2: generating a preliminary mask and a mask for cleaning with the value of the H channel respectively, where the preliminary mask may be obtained through multi-level image threshold division on the H channel, and the mask for cleaning may be obtained by multi-level image threshold division and morphological transformation operations on the H channel;

S4.3: subtracting the preliminary mask from the mask for cleaning to obtain a mask of a nucleus;

S4.4: calculating a nuclear ratio $N_t$ of each patch, where the nuclear ratio is a ratio of the number of non-zero pixels in the mask of the nucleus to the total number of pixels in the mask;

S4.5: generating a mask of a tissue area;

S4.6: calculating a tissue ratio $T_t$, where the tissue ratio is a ratio of the number of non-zero pixels in the mask of the tissue area to the total number of pixels in the entire mask;

S4.7: calculating the nuclear score $S_t$ of each patch through the nuclear score function based on the nuclear ratio and the tissue ratio of each patch;

S4.8: sorting the obtained nuclear scores, and screening the patches with the nuclear scores meeting the threshold.

In one implementation, the nuclear score function in step S4.7 may be:

$$s_t = N_t \cdot \tanh(T_t), \ 0 \leq s_t < 1,$$

where $s_t$ represents a nuclear score of a t-th patch, $N_t$ represents a nuclear ratio on the patch 1, $T_t$ represents a tissue ratio on the patch t, and the patch t represents the t-th patch.

In one implementation, the CNN classification model in step S5 may use resnet18 as a feature extraction module, and modify output of the last fully connected layer to 2.

In one implementation, in step S6, an optimal value of the model may be found according to the loss function and the gradient descent method during training, the cross-entropy loss function may be used as the loss function, and the adaptive momentum estimation algorithm (Adam) may be used as the gradient descent method.

Based on the same inventive concept, a second aspect of the present disclosure provides a system for predicting TMB in TNBC based on nuclear scores and histopathological WSIs, including:

a WSI preprocessing module, used to screen the histopathological WSIs of TNBC from histopathological images of breast cancer;

a TMB label generation module, used to calculate a TMB value of each patient according to gene mutation of each patient with TNBC, and divide the TMB values into two groups with high and low TMB according to a set threshold, denoted as TMB-H and TMB-L respectively, as a label corresponding to each WSI;

a patch screening module, used to cut the WSIs into patches of a set size and performing preprocessing, and screen patches with the nuclear scores meeting a threshold from the preprocessed patches according to a nuclear score function;

a training optimization module, used to build a CNN classification model, stochastically initialize parameters in the CNN classification model, standardize color of the patches with the nuclear scores meeting the threshold, and input the patches after color standardization and corresponding labels into the CNN classification model to train a TMB classifier, where each patch belongs to the corresponding WSI, and the label corresponding to the patch is the label of the WSI corresponding to the patch;

a TMB classification and recognition module, used to predict the TMB in the TNBC using the trained TMB classifier.

In one implementation, the system may further include: a report generation module, used to generate a visual report of prediction results and the corresponding WSI.

The foregoing one or more technical solutions in the embodiments of the present disclosure have at least one or more of the following technical effects:

According to the method for predicting TMB in TNBC based on nuclear scores and histopathological WSIs provided by the present disclosure, on the one hand, TMB in TNBC can be predicted by using histopathological images, and the conclusion of high or low TMB can be drawn, which solves the problems of high cost, complicated operation, low efficiency, and lack of universality of using WES technology to measure TMB in clinical practice. Patients with TNBC suitable for immunotherapy can be quickly screened, and patients can get earlier treatment time while reducing the workload of doctors. On the other hand, nuclei in all the patches of each WSI are graded by the nuclear score function, a higher score indicates more nuclei, some patches with a high score (that is, the patch with the nuclear score meeting the threshold) is used to train the CNN classification model, and the effective patch can be screened without relying on the pathologist to manually mark the tumor area, which improves classification accuracy while saving computing resources.

BRIEF DESCRIPTION OF THE DRAWINGS

To describe the technical solutions in embodiments of the present disclosure or in the prior art more clearly, the accompanying drawings required for describing the embodiments or the prior art will be briefly described below. Apparently, the accompanying drawings in the following description show some embodiments of the present disclosure, and those of ordinary skill in the art may still derive other drawings from these accompanying drawings without creative efforts.

DETAILED DESCRIPTION OF THE EMBODIMENTS

Figure 1:
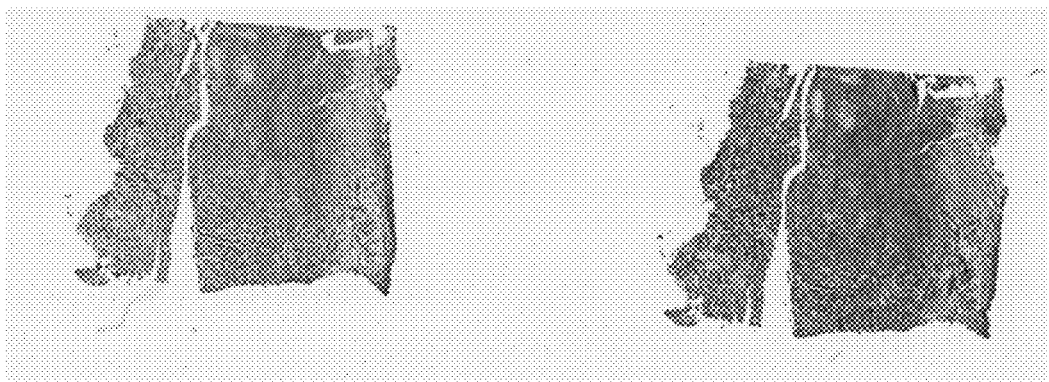
FIG. 1 shows WSI in TNBC used in an embodiment of the present disclosure.

Through a lot of research and practice, the inventors of the present disclosure have found that the clinical measurement of TMB is mainly based on the WES technology, which is high in cost, complicated in operation, time-consuming, and it is difficult to achieve in hospitals, limiting the role of immunotherapy. Therefore, it is urgent to invent an accurate, efficient, and universal TMB measurement technology. Several studies have shown that genetic mutations affect tissue morphology, which can be presented in histopathological images, and several studies have successfully predicted gene mutations from the histopathological images.

Therefore, in order to solve the problems of high cost, long time consumption, and lack of universality of TMB prediction, the present disclosure provides a method and system for automatically predicting TMB by histopathological WSIs of TNBC based on nuclear scores, which achieves the purpose of automatically drawing the conclusion of high or low TMB only using the histopathological images. The present disclosure greatly accelerates the speed of screening suitable patients with TNBC and expands the use range of measuring TMB, and assists doctors to quickly screen patients and reduces the workload of doctors. At the same time, it allows immunotherapy to play its role to a greater extent. It has important clinical significance. Based on the investigation, it is found that the present disclosure is the first invention to predict TMB in histopathological images to screen patients with TNBC suitable for immunotherapy, which is groundbreaking and forward-looking.

Although there are studies on the use of the histopathological images to predict TMB in other cancer types, there are some problems in these studies: using all patches to predict TMB is noisy, resulting in low accuracy, and patches based on tumor areas marked by pathologists are used to predict TMB, which relies too much on the labeling of the pathologist. The present disclosure solves the above problem, and the purpose of high accuracy can be achieved without the need for the pathologist to label the tumor area.

In order to make the objectives, technical solutions and advantages of the embodiments of the present disclosure clearer, the technical solutions in the embodiments of the present disclosure will be clearly and completely described below in conjunction with the accompanying drawings in the embodiments of the present disclosure. Obviously, the described embodiments are some, rather than all of the embodiments of the present disclosure. All other embodiments obtained by those of ordinary skill in the art on the basis of the embodiments of the present disclosure without creative efforts shall fall within the protection scope of the present disclosure.

Embodiment I

The embodiment of the present disclosure provides a method for predicting TMB in TNBC based on nuclear scores and histopathological WSIs, including the following steps.

S1: the histopathological WSIs of TNBC are screened from histopathological images of breast cancer.

S2: a TMB value of each patient is calculated according to gene mutation of each patient with TNBC, and the TMB values are divided into two groups with high and low TMB according to a set threshold, denoted as TMB-H and TMB-L respectively, as a label corresponding to the WSI of each patient.

S3: the WSIs are cut into patches of a set size and preprocessing is performed.

S4: patches with the nuclear scores meeting a threshold are screened from the preprocessed patches according to a nuclear score function.

S5: a CNN classification model is built, and parameters in the CNN classification model are stochastically initialized.

S6: color of the patches with the nuclear scores meeting the threshold is standardized, and the patches after color standardization and corresponding labels are input into the CNN classification model to train a TMB classifier. Each patch belongs to the corresponding WSI, and the label corresponding to the patch is the label of the WSI corresponding to the patch.

S7: the TMB in the TNBC is predicted using the trained TMB classifier.

Related terms are as follows: triple negative breast cancer (TNBC), histopathological whole slide image (WSI), tumor mutation burden (TMB), patch, TMB-H (high TMB), and TMB-L (low TMB).

It should be noted that a patient may correspond to one or more WSIs, and the WSIs of the same patient correspond to only one group. For example, it is assumed that a patient with TMB-H has two WSIs, both of which are TMB-H.

In the specific implementation process, patients with TNBC can be screened according to the positive or negative status of ER, PR, and HER2 of the patient. When ER, PR, and HER2 are all negative, the patient is with TNBC.

Figure 4:
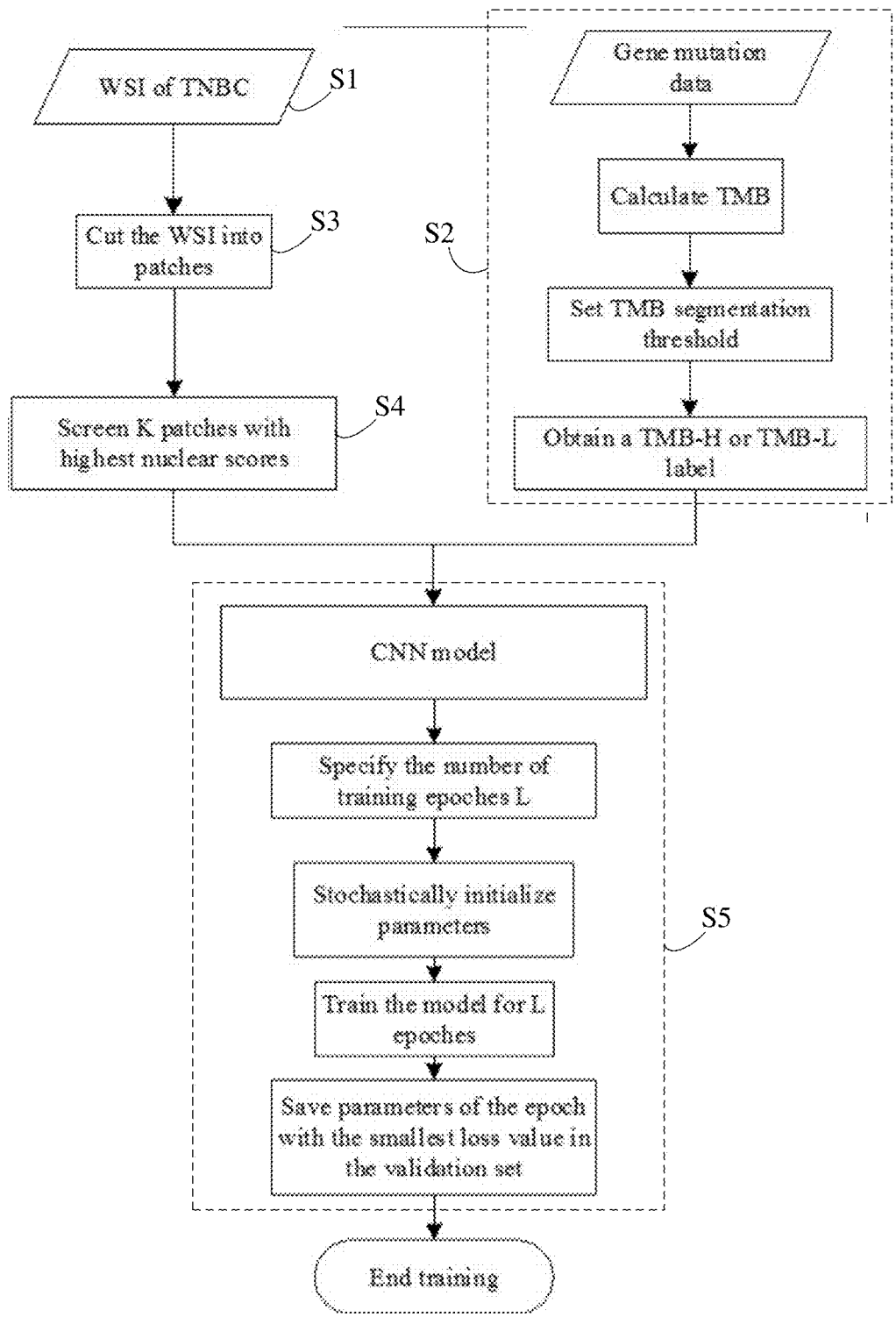
FIG. 4 is a work flow chart of a method for predicting TMB in TNBC based on nuclear scores and histopathological WSIs provided by the embodiment of the present disclosure.

FIG. 4 is a work flow chart of a method for predicting TMB in TNBC based on nuclear scores and histopathological WSIs provided by the embodiment of the present disclosure. FIG. 1 shows WSI in TNBC used in a specific embodiment.

In the specific application process, the present disclosure uses a method for automatically predicting TMB in TNBC based on nuclear scores and histopathological WSIs, which realizes the use of the histopathological images to screen patients with TNBC suitable for immunotherapy, and solves the problem of high cost and poor universality of screening patients using the WES technology to detect TMB in clinic, greatly improving the detection speed of TMB, and facilitates the advancement of immunotherapy.

In one implementation, a process of calculating a TMB value of each patient according to gene mutation of each patient with TNBC in step S2 includes: dividing tumors with nonsynonymous mutations in a somatic protein coding region of the patient by a total length of the protein coding region to obtain the TMB value of each patient, in mutations/mb, to characterize a density of distribution of nonsynonymous mutations in the protein coding region.

In one implementation, when the TMB values are divided into two groups with high and low TMB in step S2, a median division method is used, and the threshold is recorded as M. When the TMB value of the patient is greater than M, the patient is in the TMB-H group, otherwise, the patient is in the TMB-L group.

In one implementation, step S3 includes the following steps.

First, the number of layers of WSI is selected, and the images of the set size are saved successively based on this layer, so as to cut the image into patches.

Blank and irregular patches are removed from the cut patches. A method for removing the blank patches is: calculating a pixel mean of each patch, and when the pixel mean of the patch is less than the set threshold, retaining the patch, otherwise discarding the patch. A method for removing the irregular patches is: calculating whether each patch has a length and width equal to a set patch size, and if the length and width are equal to the set patch size, retaining the patch, otherwise discarding the patch.

Figure 2:
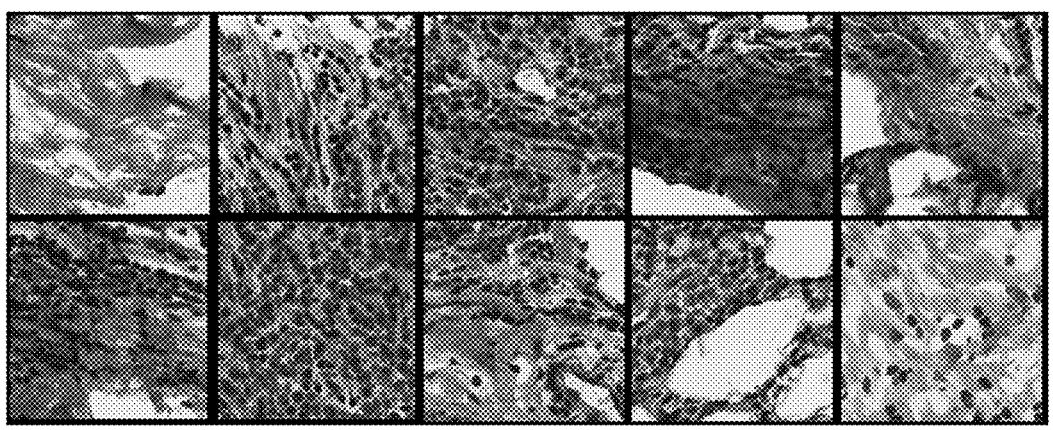
FIG. 2 is a diagram of patches partially cut in the embodiment of the present disclosure.

FIG. 2 is a diagram of patches partially cut in the embodiment of the present disclosure.

In one implementation, step S4 includes the following steps.

S4.1: an RGB image is converted to HED space and a value of an H channel is extracted.

S4.2: a preliminary mask and a mask for cleaning are generated with the value of the H channel respectively. The preliminary mask is obtained through multi-level image threshold division on the H channel, and the mask for cleaning is obtained by multi-level image threshold division and morphological transformation operations on the H channel.

S4.3: the preliminary mask is subtracted from the mask for cleaning to obtain a nucleus mask.

S4.4: a nuclear ratio $N_t$ of each patch is calculated. The nuclear ratio is a ratio of the number of non-zero pixels in the mask of the nucleus to the total number of pixels in the mask.

S4.5: a mask of a tissue area is generated.

S4.6: a tissue ratio $T_t$ is calculated. The tissue ratio is a ratio of the number of non-zero pixels in the mask of the tissue area to the total number of pixels in the entire mask.

S4.7: the nuclear score $s_t$ of each patch is calculated through the nuclear score function based on the nuclear ratio and the tissue ratio of each patch.

S4.8: the obtained nuclear scores are sorted, and the patches with the nuclear scores meeting the threshold are screened.

Figure 5:
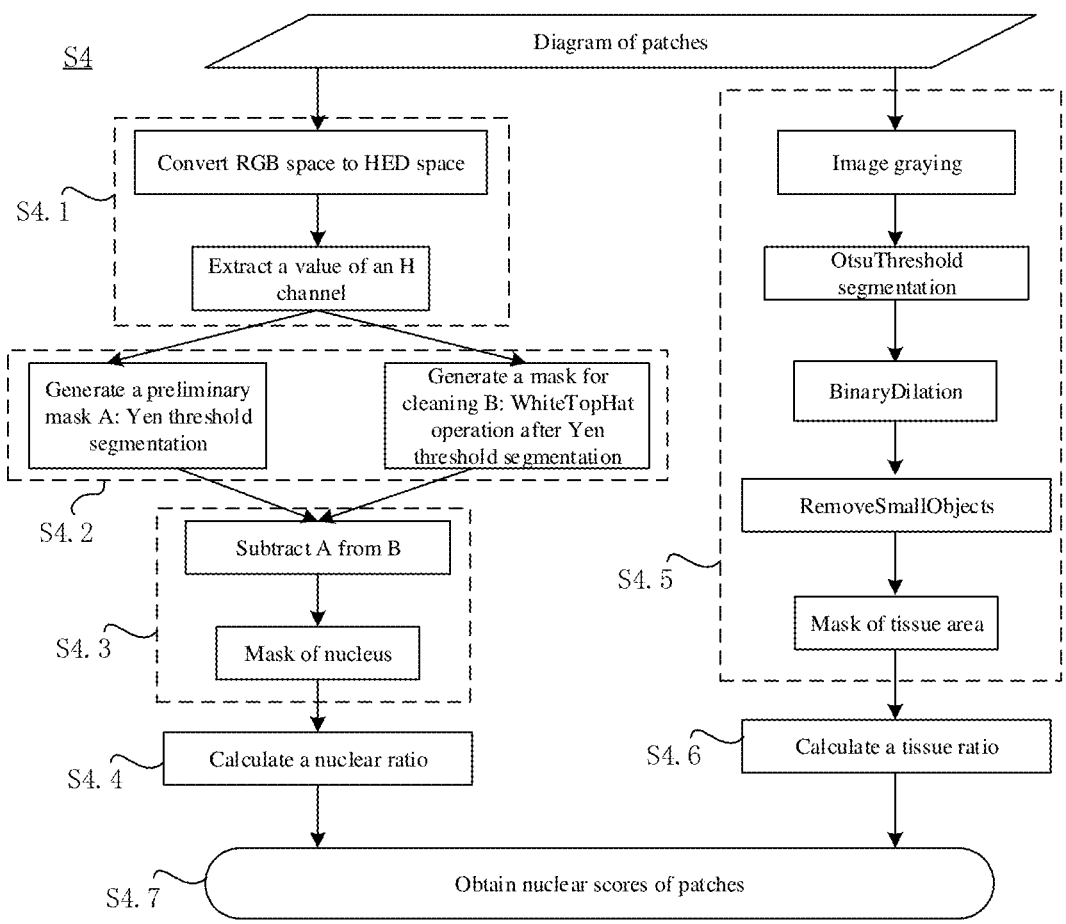
FIG. 5 is a specific flow chart of screening patches using the nuclear score function in the embodiment of the present disclosure.
Figure 6:
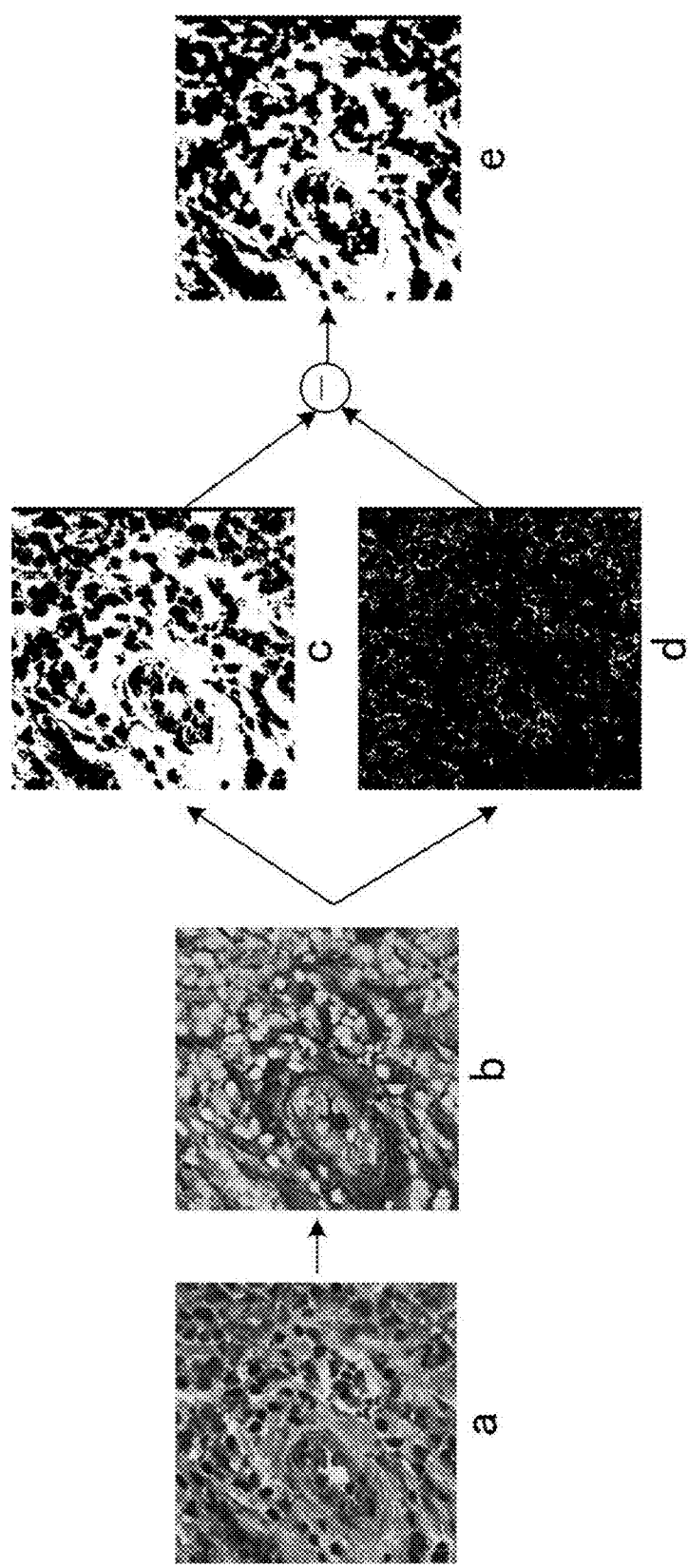
FIG. 6 is a schematic diagram of a generation process of nucleus mask in the nuclear score function in the embodiment of the present disclosure.
Figure 7:
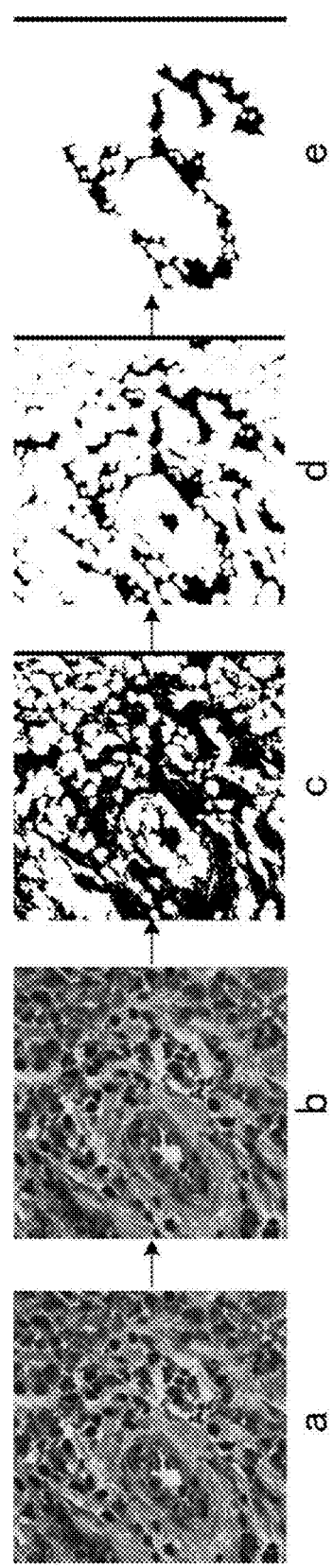
FIG. 7 is a schematic diagram of a generation process of a tissue area mask in the nuclear score function in the embodiment of the present disclosure.

Referring to FIG. 5 to FIG. 7, FIG. 5 is a specific flow chart of screening patches using the nuclear score function in the embodiment of the present disclosure. FIG. 6 is a schematic diagram of a generation process of a nucleus mask in the nuclear score function in the embodiment of the present disclosure. FIG. 7 is a schematic diagram of a generation process of a tissue area mask in the nuclear score function in the embodiment of the present disclosure. In FIG. 6, a represents an original image, b represents conversion of RGB space to HED space and extraction of H channel information, c represents Yen threshold segmentation, d represents the WhiteTopHat operation after Yen threshold segmentation, and e represents an obtained mask of the nucleus. In FIG. 7, a represents an original image, b represents conversion of RGB space to grayscale space, c represents OtsuThreshold segmentation, d represents BinaryDilation, and e represents RemoveSmallObjects and the image is a tissue area mask. In the specific implementation process, in step S4.2, the YenThreshold method may be used for the multi-level image threshold division, and the TopHat algorithm may be used for the morphological transformation. (In order to show the WSI, the patch, the mask of the nucleus, and the mask of the tissue area more clearly, reference may be made to the actual review reference for the original image of the related drawings)

In step S4.5, during generation of the mask of the tissue area, the RGB image is mainly converted into a grayscale image, and then OtsuThreshold, BinaryDilation, and RemoveSmallObjects operations are performed on the grayscale image.

Specifically, YenThreshold segmentation is a multi-level image threshold method used to separate objects from the background. For a given gray level s, a threshold that maximizes the entropy-related EC is automatically calculated, defined as:

$$EC(s)=-\ln[G(s) \times G'(s)]+2\ln[P(s) \times (1-P(s))]$$

G(s) represents the sum of squares of probability up to the (s−1)-th gray level, $$G(s) = \sum_{i=0}^{s-1} p_i^2, \; G'(s) = \sum_{i=s}^{m-1} p_i^2,$$

where m is the number of gray levels in the image and i refers to the i-th gray level.

$$P(s) = \sum_{i=0}^{s-1} p_i$$

represents the total probability up to the (s−1)-th gray level, and the probability of the gray level i in the image f can be calculated as $$p_i = \frac{f_i}{N \times N},$$

where $f_i$ is the image of the i-th gray level, and N×N represents pixels of the image of the i-th gray level. In the maximum entropy criterion, the basic idea is to choose a threshold that maximizes the total amount of information provided by the object and background. In order to obtain the maximum correlation of object and background contributions in the image f, EC(s) is maximized, and thus a threshold s* is determined, such that $$EC(s^*) = \max_{s \in G_m} EC(s),$$

where $G_m$ represents the set of gray levels.

The TopHat algorithm belongs to morphological transformation and is mainly used to solve the problem of uneven background grayscale caused by uneven illumination. The TopHat algorithm is essentially a combination of opening and closing operations in morphological transformation: the opening operation can eliminate brighter details in grayscale images, and the closing operation can eliminate darker details. WhiteTopHat is the result of the original image-opening operation, the WhiteTopHat of an image is defined as the image minus its morphological opening relative to the structuring element, and this operation returns the bright spots in the image that are smaller than the structuring element.

The basic idea of OtsuThreshold is to use a threshold to divide the data in the image into two categories. In one category, the gray level of the pixels of the image is less than this threshold, and in the other category, the gray level of the pixels of the image is greater than or equal to this threshold. If the variance of the gray levels of the pixels in these two categories is larger, it means that the obtained threshold is the best threshold, and the image can be divided into two parts, the foreground and the background, by using the threshold. The objective function is:

$$l(v)=W_0*(U_0-U)+W_1*(U_1-U)^2.$$

l(v) is the inter-class variance when the segmentation threshold is v. $W_0$ represents the proportion of foreground pixels in the image and the mean is $U_0$, and $W_1$ represents the proportion of background pixels in the image and the mean is $U_1$. The mean of the entire image is $U=W_0*U_0+W_1*U_1$, and the corresponding v is the optimal threshold when the Otsu algorithm makes l(v) the maximum.

BinaryDilation is a dilation operation on a binary image. Dilation operation on a binary image requires an SE kernel, which consists of a binary matrix, and an origin is defined to represent the core of the kernel. The specific steps are to traverse each pixel of the original image, aligning it with the origin of the SE kernel, and then take the maximum value of the corresponding pixels in the original image covered by all 1 positions in the current SE, and replace the current pixel value with this maximum value (the maximum value of the binary image is 1).

The RemoveSmallHoles operation effectively removes the noise in the image by setting the threshold of the connected domain area, that is, removes the small connected areas.

After calculation, the obtained nuclear scores $s_t$ are sorted, and finally a certain number of patches at the top are selected.

In one implementation, the nuclear score function in step S4.7 is:

$$s_t=N_t \cdot \tanh(T_t), \; 0 \leq s_t < 1$$

$s_t$ represents a nuclear score of a t-th patch, $N_t$ represents a nuclear ratio on the patch t, $T_t$ represents a tissue ratio on the patch t (that is, the part of the tissue on the patch t) and the patch t represents the t-th patch.

Figure 3:
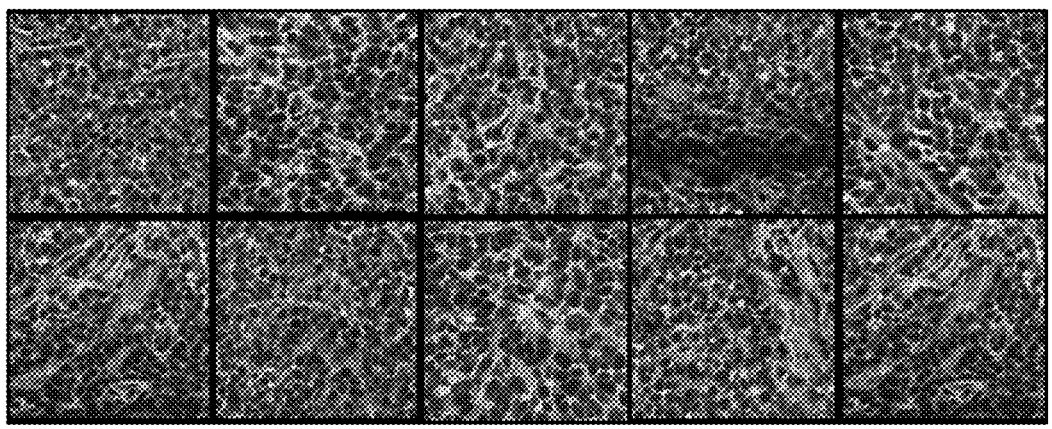
FIG. 3 is a diagram of some patches screened using a nuclear score function in the embodiment of the present disclosure.

FIG. 3 is a diagram of some patches screened using a nuclear score function in the embodiment of the present disclosure.

In one implementation, the CNN classification model in step S5 uses resnet18, which is a CNN having an eighteen-layer architecture that is trained on a database containing lots of images, as a feature extraction module, and modifies output of the last fully connected layer to 2.

Specifically, the main idea of resnet18 is residual learning. The objective function includes two parts: the identity function and the residual function. The formula is as follows:

$$h(x)=x+(h(x)-x)$$

h(x) represents the objective function, and x represents the identity function, and h(x)−x represents the residual function. The ReLU activation function is:

$$f(x)=\max(0,x)$$

x represents the input of neurons, which can change all negative values into 0, while the positive values remain unchanged. This unilateral inhibition function can make the neurons in the neural network have sparse activation.

In one implementation, in step S6, an optimal value of the model is found according to the loss function and the gradient descent method during training. The cross-entropy loss function is used as the loss function, and the adaptive momentum estimation algorithm (Adam) is used as the gradient descent method.

In the specific implementation process, the optimal value of the model is found according to the loss function and the gradient descent method during training. The loss function is used to quantify the difference between the model prediction and the real label, and the gradient descent is used to find a set of parameters that can minimize the structural risk. The cross-entropy loss function is used as the loss function, and its function is:

$$J = -[y \log \hat{y} + (1-y) \log(1-\hat{y})]$$

y represents the real label with the value of 0 or 1, and $\hat{y}$ represents the probability that the sample is predicted to be positive. A greater difference between the predicted output and y indicates a greater value of J.

The adaptive momentum estimation algorithm, namely Adam, is used as the gradient descent method, which is a combination of the momentum method and RMSprop. It not only uses momentum as the update direction of parameters, but also can adaptively adjust the learning rate. The main idea of the momentum method is to replace each actual gradient with the accumulated momentum, which can effectively alleviate the vibration in the process of gradient descent which seriously affects the optimization speed. In the t-th iteration, the update direction of the parameters is:

$$\Delta\theta_t = \rho\Delta\theta_{t-1} - \alpha g_t,$$

$\Delta\theta_t$ represents the update difference of the t-th iteration, and $\Delta\theta_{t-1}$ represents the update difference of the (t−1)-th iteration. β is the momentum factor, α is the learning rate, and $g_t$ represents the gradient of the update. The actual update difference of each parameter depends on the weighted average of gradient in recent period of time. Adam not only uses momentum as the update direction of the parameters, but also can adaptively adjust the learning rate. Specifically, the exponentially weighted average of the square $g_t^2$ of the gradient is calculated, and the exponentially weighted average of the gradient $g_T$ is calculated. The relevant formula is:

$$M_T = \beta_1 M_{t-1} + (1-\beta_1)g_t, \text{ and}$$

$$G_t = \beta_2 G_{t-1} + (1-\beta_2)g_t \Box g_t.$$

$M_t$ can be regarded as the mean (first moment) of the gradient, and $G_t$ can be regarded as the variance (second moment) of the gradient without subtracting the mean. $\beta_1$ and $\beta_2$ are the decay rates of the two moving averages respectively, and $g_t$ represents the gradient of the update, calculated as:

$$\hat{M}_t = \frac{M_t}{1-\beta_1^t}, \text{ and}$$

$$\hat{G}_t = \frac{G_t}{1-\beta_2^t}.$$

$\hat{M}_t$ is the bias correction for the $\hat{M}_t$, and $\hat{G}_t$ is the bias correction for the $G_t$. $\beta_1^t$ and $\beta_2^t$ represent the decay rate of the two moving averages of the t-th iteration respectively. ε is a very small number, and the parameter update difference $\Delta\theta t$ of Adam is:

$$\Delta\theta t = -\frac{\alpha}{\sqrt{\hat{G}_t} + \varepsilon}\hat{M}_t.$$

The training process is as follows: the number of train epochs L is specified, the Adam optimizer is used for gradient descent calculation, training is performed for L epochs in total, and the parameters and results of the epoch with the smallest loss value in a validation set are obtained.

The method for predicting TMB in TNBC based on nuclear scores and histopathological WSIs provided by the present disclosure will be introduced below through specific examples.

Step I: the histopathological WSIs of TNBC are screened from histopathological images of breast cancer. The number of patients with TNBC is recorded as a, and the number of the histopathological WSIs of TNBC is recorded as b.

Step II: a TMB value of each patient is calculated according to gene mutation of each patient with TNBC, and the TMB values are divided into two groups with high and low TMB according to a set threshold, denoted as TMB-H and TMB-L respectively, as a label corresponding to each WSI.

Step III: the histopathological WSIs of TNBC are cut into patches of 512*512, and blank and irregular patches are removed.

Step IV: K patches with the highest nuclear scores corresponding to each WSI are screened from the patches obtained in step III according to a nuclear score function.

Step V: a CNN classification model is built and recorded as a model A, and parameters in the model A are stochastically initialized.

Step VI: color of the patches screened in step IV is standardized, and the patches after color standardization and corresponding labels obtained in step II are input into the model A to train a TMB classifier. The number of train epochs is specified as L.

Step VII: high or low TMB of each WSI is predicted using the trained TMB classifier.

In the specific implementation process, according to the positive or negative status screening of ER, PR, and HER2 of the patient. When ER, PR, and HER2 are all negative, the patient is with TNBC. The data set used in the present disclosure comes from the breast cancer data set TCGA_BRCA of the TCGA database, and the information of the ER, PR, and HER2 of the patient is obtained according to the clinical information. The number of screened patients a is 74, and the number of histopathological WSIs of TNBC b is 87.

In this implementation, single nucleotide variants (SNV) data is used as gene mutation data. The median division method is used for TMB threshold division, the threshold M is 0.98, and when the TMB value of the patient is greater than M, the patient is in the TMB-H group, otherwise, the patient is in the TMB-L group.

In step III, the histopathological WSIs of TNBC are cut into 512*512 patches. First, the 0-th layer of WSI is selected to be cut into patches. Based on this layer, images of a 512*512 size will be saved successively, so as to achieve the purpose of dividing the image into patches, and finally removing some blank and irregular patches.

A method for determining whether the patch is a blank patch is: calculating a pixel mean of each patch, and when the pixel mean of the patch is less than 235, retaining the patch, otherwise discarding the patch. A method for determining whether the patch is an irregular patch is: calculating whether each patch has a length and width equal to 512, and if they are equal, retaining the patch, otherwise discarding the patch.

In step IV, according to the nuclear score function, K patches with the highest corresponding nuclear scores are screened from the preprocessed patches in the patches obtained in step III. In the present disclosure, the value of K is 100.

During training of the TMB classifier, in this implementation, the number of train epochs L is 50, and the Adam optimizer is used for gradient descent calculation. The learning rate adopts exponential decay, the initial learning rate is 0.001, and the batch_size value is 16. After L epochs of training, the parameters and results of the epoch with the smallest loss value in the validation set are obtained.

In view of the problems of high cost, long time consumption, and lack of universality in clinical measurement of TMB, which leads to low efficiency in screening patients with TNBC suitable for immunotherapy, the present disclosure provides the method and system for predicting TMB in TNBC based on nuclear scores and histopathological WSIs, which achieves the purpose of automatically drawing the conclusion of high or low TMB only using the histopathological images, and can accurately and efficiently screen patients with TNBC suitable for immunotherapy. The present disclosure greatly accelerates the speed of screening of suitable patients with TNBC and expands the use range of measuring TMB, and assists doctors to quickly screen patients, reducing the workload of doctors. It allows immunotherapy to play its role to a greater extent at the same time. It has important clinical significance. Table 1 shows performance comparison between patches screened with the nuclear score function and the TMB classifier trained with all the patches in the present disclosure.

TABLE 1

Performance comparison between all patches and nuclear patches

|  | Accuracy of test set | Test set F1 |
| --- | --- | --- |
| All patches | 50% | 50% |
| Nuclear patches | 81.25% | 76.92% |

Compared with the prior art, the present disclosure has the following beneficial effects:

1. In the present disclosure, high or low TMB can be predicted by using histopathological images, which solves the problems of high cost, complicated operation, low efficiency, and lack of universality of using WES technology to measure TMB in clinical practice. Patients with TNBC suitable for immunotherapy can be quickly screened, and patients can get earlier treatment time while reducing the workload of doctors.

2. In the present disclosure, nuclei in all the patches of each WSI are graded by the nuclear score function. A higher score indicates more nuclei. Some patches with a high score is used to train the CNN classification model, and the effective patch can be screened without relying on the pathologist to manually label the tumor area, which improves classification accuracy while saving computing resources.

Embodiment II

Based on the same inventive concept, the present embodiment provides a system for predicting TMB in TNBC based on nuclear scores and histopathological WSIs, including: a WSI preprocessing module 801, a TMB label generation module 802, a patch screening module 803, a training optimization module 804, and a TMB classification and recognition module 805.

The WSI preprocessing module 801 is used to screen the histopathological WSIs of TNBC from histopathological images of breast cancer.

The TMB label generation module 802 is used to calculate a TMB value of each patient according to gene mutation of each patient with TNBC, and divide the TMB values into two groups with high and low TMB according to a set threshold, denoted as TMB-H and TMB-L respectively, as a label corresponding to each WSI.

The patch screening module 803 is used to cut the WSIs into patches of a set size and performing preprocessing, and screen patches with the nuclear scores meeting a threshold from the preprocessed patches according to a nuclear score function.

The training optimization module 804 is used to build a CNN classification model, stochastically initialize parameters in the CNN classification model. Standardizing color of the patches with the nuclear scores meeting the threshold, and input the patches after color standardization and corresponding labels into the CNN classification model to train a TMB classifier. Each patch belongs to the corresponding WSI, and the label corresponding to the patch is the label of the WSI corresponding to the patch.

The TMB classification and recognition module 805 is used to predict the TMB in the TNBC using the trained TMB classifier.

In one implementation, the system further includes: a report generation module, used to generate a visual report of prediction results and the corresponding WSI for reference by doctors.

Figure 8:
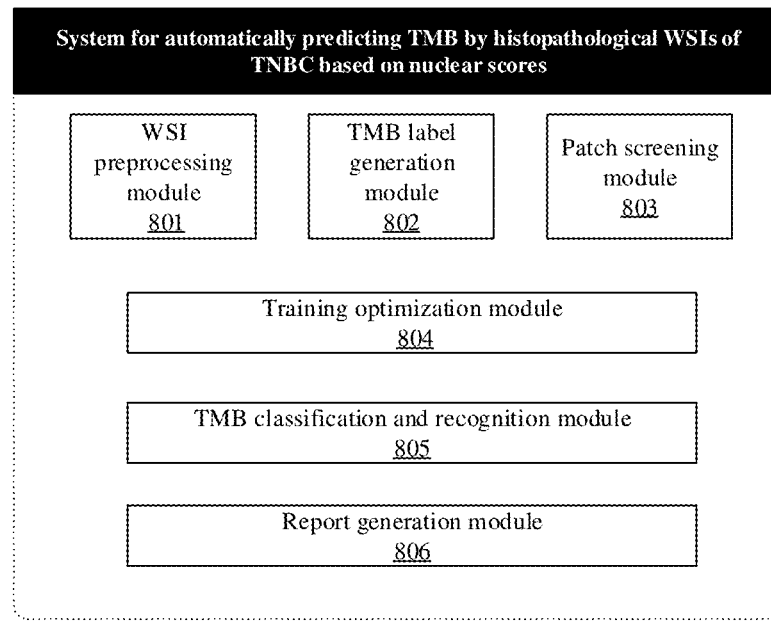
FIG. 8 is a modular structure diagram of a system for predicting TMB in TNBC based on nuclear scores and histopathological WSIs in the embodiment of the present disclosure.

FIG. 8 is a modular structure diagram of the system for predicting TMB in TNBC based on nuclear scores and histopathological WSIs in the embodiment of the present disclosure.

Since the system introduced in Embodiment II of the present disclosure is the system used to implement the method for predicting TMB in TNBC based on nuclear scores and histopathological WSIs in Embodiment I of the present disclosure, based on the method introduced in Embodiment I of the present disclosure, those skilled in the art can understand the specific structure and modification of the system, so it is not repeated here. All systems used in the method of Embodiment I of the present disclosure belong to the scope of protection of the present disclosure.

In addition, it should also be noted herein that the respective composite parts in the above system can be configured by software, firmware, hardwire or a combination thereof. Specific means or manners that can be used for the configuration will not be stated repeatedly herein since they are well-known to those skilled in the art. In case of implementation by software or firmware, programs constituting the software are installed from a storage medium or a network to a computer (e.g. the universal computer 900 as shown in FIG. 9) having a dedicated hardware structure: the computer, when installed with various programs, can implement various functions and the like.

Figure 9:
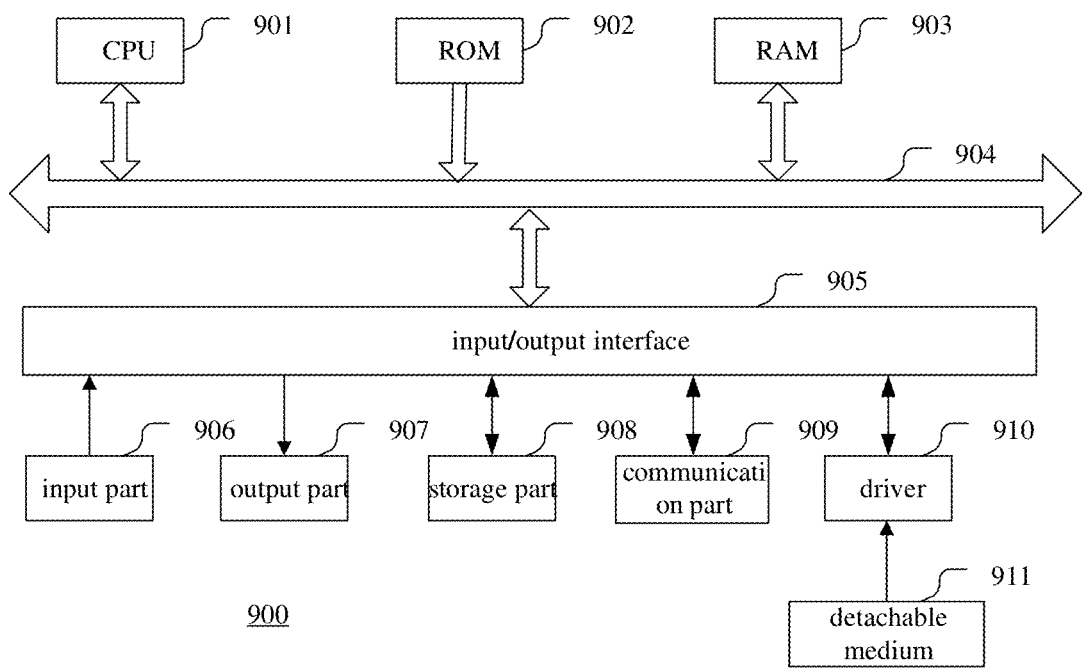
FIG. 9 is a schematic block diagram of a computer which is used for implementing the method and the system according to the embodiments of the present disclosure.

FIG. 9 shows a schematic block diagram of a computer that can be used for implementing the method and the system according to the embodiments of the present disclosure.

In FIG. 9, a central processing unit (CPU) 901 executes various processing according to a program stored in a read-only memory (ROM) 902 or a program loaded from a storage part 908 to a random access memory (RAM) 903. In the RAM 903, data needed at the time of execution of various processing and the like by the CPU 901 is also stored according to requirements. The CPU 901, the ROM 902 and the RAM 903 are connected to each other via a bus 904. An input/output interface 905 is also connected to the bus 904.

The following components are connected to the input/output interface 905: an input part 906 (including a keyboard, a mouse and the like); an output part 907 (including a display, such as a Cathode Ray Tube (CRT), a Liquid Crystal Display (LCD) and the like, as well as a loudspeaker and the like); the storage part 908 (including a hard disc and the like); and a communication part 909 (including a network interface card such as an LAN card, a modem and so on). The communication part 909 performs communication processing via a network such as the Internet. According to requirements, a driver 910 may also be connected to the input/output interface 905. A detachable medium 911 such as a magnetic disc, an optical disc, a magnetic optical disc, a semiconductor memory and the like may be installed on the driver 910 according to requirements, such that a computer program read therefrom is installed in the storage part 908 according to requirements.

In the case of carrying out the foregoing series of processing by software, programs constituting the software are installed from a network such as the Internet or a storage medium such as the detachable medium 911.

Those skilled in the art should appreciate that such a storage medium is not limited to the detachable medium 911 storing therein a program and distributed separately from the apparatus to provide the program to a user as shown in FIG. 9. Examples of the detachable medium 911 include a magnetic disc (including floppy disc), a compact disc (including compact disc read-only memory (CD-ROM) and digital versatile disc (DVD), a magneto optical disc (including mini disc (MD)), and a semiconductor memory. Or, the storage medium may be hard discs and the like included in the ROM 902 and the storage part 908 in which programs are stored, and are distributed concurrently with the apparatus including them to users.

The present disclosure further proposes a program product storing therein a machine-readable instruction code that, when read and executed by a machine, can implement the aforesaid method according to the embodiment of the present disclosure.

Correspondingly, a storage medium for carrying the program product storing therein the machine-readable instruction code is also included in the disclosure of the present disclosure. The storage medium includes but is not limited to a floppy disc, an optical disc, a magnetic optical disc, a memory card, a memory stick and the like. The foregoing embodiments are only used to explain the technical solutions of the present disclosure, and are not intended to limit the same. Although the present disclosure is described in detail with reference to the foregoing embodiments, those of ordinary skill in the art should understand that they can still modify the technical solutions described in the foregoing embodiments, or make equivalent substitutions on some technical features therein. These modifications or substitutions do not make the essence of the corresponding technical solutions deviate from the spirit and scope of the technical solutions of the embodiments of the present disclosure.

What is claimed is:

1. A method for predicting tumor mutation burden (TMB) in triple-negative breast cancer (TNBC) based on nuclear scores and histopathological whole slide images (WSIs), comprising the following steps:
    S1: screening the histopathological WSIs of TNBC from histopathological images of breast cancer;
    S2: calculating a TMB value of each patient according to gene mutation of each patient with TNBC, and dividing the TMB values into two groups with high and low TMB according to a set threshold, denoted as TMB-H group and TMB-L group respectively, as a label corresponding to the WSI of each patient;
    S3: dividing the WSIs into patches of a set size and performing preprocessing;
    S4: screening patches with the nuclear scores meeting a threshold from the preprocessed patches according to a nuclear score function;
    S5: building a convolutional neural network (CNN) classification model, and stochastically initializing parameters in the CNN classification model;
    S6: standardizing color of the patches with the nuclear scores meeting the threshold, and inputting the patches after color standardization and corresponding labels into the CNN classification model to train a TMB classifier, wherein each patch belongs to the corresponding WSI, and the label corresponding to the patch is the label of the WSI corresponding to the patch;
    S7: predicting the TMB in the TNBC using the trained TMB classifier.

2. The method for predicting TMB in TNBC according to claim 1, wherein a process of calculating a TMB value of each patient according to gene mutation of each patient with TNBC in step S2 comprises: dividing tumors with nonsynonymous mutations in a somatic protein coding region of the patient by a total length of the protein coding region to obtain the TMB value of each patient, in mutations/mb, to characterize a density of distribution of nonsynonymous mutations in the protein coding region.

3. The method for predicting TMB in TNBC according to claim 1, wherein when the TMB values are divided into two groups with high and low TMB in step S2, a median division method is used, and the threshold is recorded as M, and when the TMB value of the patient is greater than M, the patient is in the TMB-H group, otherwise, the patient is in the TMB-L group.

4. The method for predicting TMB in TNBC according to claim 1, wherein step S3 comprises:
    first, selecting the number of layers of WSI, and saving the images of the set size successively based on this layer, so as to cut the image into patches;
    second, removing blank and irregular patches from the cut patches, wherein a method for removing the blank patches is: calculating a pixel mean of each patch, and when the pixel mean of the patch is less than the set threshold, retaining the patch, otherwise discarding the patch; a method for removing the irregular patches is: calculating whether each patch has a length and width equal to a set patch size, and if the length and width are equal to the set patch size, retaining the patch, otherwise discarding the patch.

5. The method for predicting TMB in TNBC according to claim 1, wherein step S4 comprises:
    S4.1: converting an RGB image to Holistically-Nested Edge Detection (HED) space and extracting a value of an Hue (H) channel;
    S4.2: generating a preliminary mask and a mask for cleaning with the value of the H channel respectively, wherein the preliminary mask is obtained through multi-level image threshold division on the H channel, and the mask for cleaning is obtained by multi-level image threshold division and morphological transformation operations on the H channel;
    S4.3: subtracting the preliminary mask from the mask for cleaning to obtain a nucleus mask;

S4.4: calculating a nuclear ratio $N_t$ of each patch, wherein the nuclear ratio is a ratio of the number of non-zero pixels in the mask of the nucleus to the total number of pixels in the mask;

S4.5: generating a mask of a tissue area;

S4.6: calculating a tissue ratio $T_t$, wherein the tissue ratio is a ratio of the number of non-zero pixels in the mask of the tissue area to the total number of pixels in the entire mask;

S4.7: calculating the nuclear score $s_t$ of each patch through the nuclear score function based on the nuclear ratio and the tissue ratio $T_t$ of each patch;

S4.8: sorting the obtained nuclear scores, and screening the patches with the nuclear scores meeting the threshold.

6. The method for predicting TMB in TNBC according to claim 5, wherein the nuclear score function in step S4.7 is:

$$s_t = N_t \tanh(T_t), \quad 0 \le s_t < 1$$

wherein $s_t$ represents a nuclear score of a 1-th patch, and $N_t$ represents a nuclear ratio on the patch t, $T_t$ represents a tissue ratio on the patch t, and the patch t represents the t-th patch.

7. The method for predicting TMB in TNBC according to claim 1, wherein the CNN classification model in step S5 uses a CNN having an eighteen-layer architecture, as a feature extraction module, and modifies output of the last fully connected layer to 2.

8. The method for predicting TMB in TNBC according to claim 1, wherein in step S6, an optimal value of the model is found according to the loss function and the gradient descent method during training, the cross-entropy loss function is used as the loss function, and the adaptive momentum estimation algorithm (Adam) is used as the gradient descent method.

9. A system for predicting tumor mutation burden (TMB) in triple-negative breast cancer (TNBC) based on nuclear scores and histopathological whole slide images (WSIs), comprising a processor and a memory storing program codes, wherein the processor performs the stored program codes to:

screen the histopathological WSIs of TNBC from histopathological images of breast cancer;

calculate a TMB value of each patient according to gene mutation of each patient with TNBC, and divide the TMB values into two groups with high and low TMB according to a set threshold, denoted as TMB-H group and TMB-L group respectively, as a label corresponding to each WSI;

cut the WSIs into patches of a set size and performing preprocessing, and screen patches with the nuclear scores meeting a threshold from the preprocessed patches according to a nuclear score function;

build a CNN classification model, stochastically initialize parameters in the CNN classification model, and standardize color of the patches with the nuclear scores meeting the threshold, and input the patches after color standardization and corresponding labels into the CNN classification model to train a TMB classifier, wherein each patch belongs to the corresponding WSI, and the label corresponding to the patch is the label of the WSI corresponding to the patch;

predict the TMB in the TNBC using the trained TMB classifier.

10. The system for predicting TMB in TNBC according to claim 9, wherein the processor further performs the stored program codes to generate a visual report of prediction results and the corresponding WSI.

* * * * *